US011045414B2

(12) United States Patent
Murray et al.

(10) Patent No.: US 11,045,414 B2
(45) Date of Patent: Jun. 29, 2021

(54) TOPICAL MOSQUITO CONTROL PRODUCT

(71) Applicant: Penta 5 USA, LLC, Sarasota, FL (US)

(72) Inventors: R. Charles Murray, Sarasota, FL (US); John Harlin, Sarasota, FL (US)

(73) Assignee: Penta 5 USA, LLC, Sarasota, FL (US)

( * ) Notice: Subject to any disclaimer, the term of this patent is extended or adjusted under 35 U.S.C. 154(b) by 757 days.

(21) Appl. No.: 15/656,660

(22) Filed: Jul. 21, 2017

(65) Prior Publication Data

US 2017/0319465 A1 Nov. 9, 2017

Related U.S. Application Data

(63) Continuation-in-part of application No. 15/412,706, filed on Jan. 23, 2017.

(60) Provisional application No. 62/416,457, filed on Nov. 2, 2016, provisional application No. 62/281,347, filed on Jan. 21, 2016.

(51) Int. Cl.
| | |
|---|---|
| *A61K 8/92* | (2006.01) |
| *A61Q 17/02* | (2006.01) |
| *A01N 25/04* | (2006.01) |
| *A01N 65/06* | (2009.01) |
| *A01N 65/12* | (2009.01) |
| *A01N 25/10* | (2006.01) |
| *A01N 65/20* | (2009.01) |
| *A01N 65/24* | (2009.01) |
| *A01N 25/02* | (2006.01) |
| *A01N 65/00* | (2009.01) |

(52) U.S. Cl.
CPC .............. *A61K 8/922* (2013.01); *A01N 25/02* (2013.01); *A01N 25/04* (2013.01); *A01N 25/10* (2013.01); *A01N 65/00* (2013.01); *A01N 65/06* (2013.01); *A01N 65/12* (2013.01); *A01N 65/20* (2013.01); *A01N 65/24* (2013.01); *A61Q 17/02* (2013.01); *Y02A 50/30* (2018.01)

(58) Field of Classification Search
CPC ........ A61K 36/54; A61K 36/48; A61K 36/15; A61K 36/28; A61K 36/899; A61K 8/922; A01N 49/00; A01N 65/06; A01N 65/00; A01N 65/24; A01N 65/20; A01N 25/02; A01N 25/04; A01N 25/10; A01N 65/12; A61Q 17/02; Y02A 50/327; Y02A 50/338; Y02A 50/339; Y02A 50/348; Y02A 50/30

USPC .......................... 424/757, 770, 750, 739, 764
See application file for complete search history.

(56) References Cited

U.S. PATENT DOCUMENTS

| | | |
|---|---|---|
| D262,942 S | 2/1982 | DiPisa, Sr. |
| D263,074 S | 2/1982 | Mason |
| D375,352 S | 11/1996 | Bologna |
| D467,336 S | 12/2002 | Gilbard et al. |
| D492,407 S | 6/2004 | Masuda et al. |
| D498,666 S | 11/2004 | Mitchell |
| D539,903 S | 4/2007 | Strong |
| D618,339 S | 6/2010 | Hansen |
| 7,832,601 B2 | 11/2010 | Zahn et al. |
| D663,414 S | 7/2012 | Robin |
| D666,289 S | 8/2012 | DeCoste |
| D674,481 S | 1/2013 | DeCoste |
| D681,196 S | 4/2013 | Henrikson et al. |
| D684,259 S | 6/2013 | Mehta |
| D703,063 S | 4/2014 | Garrity et al. |
| D710,993 S | 8/2014 | DeCoste, Jr. |
| D721,434 S | 1/2015 | Mulvey et al. |
| D753,292 S | 4/2016 | Oates, II et al. |
| 9,326,524 B1 | 5/2016 | Jack et al. |
| D779,653 S | 2/2017 | Habig et al. |
| D805,212 S | 12/2017 | Crumitie |
| 2007/0042182 A1* | 2/2007 | Markus .................. A01N 25/28 428/402.2 |
| 2007/0140998 A1* | 6/2007 | Kato .................... C07F 9/65515 424/62 |
| 2007/0219515 A1 | 9/2007 | Marsh et al. |
| 2009/0169656 A1 | 7/2009 | Porter et al. |
| 2014/0242199 A1 | 8/2014 | Manhas et al. |

FOREIGN PATENT DOCUMENTS

WO     2014/116022 A1     7/2014

OTHER PUBLICATIONS

Caroline Cox, "Plant-Based Mosquito Repellents: Making A Careful Choice", Journal of Pesticide Reform/Fall 2005, vol. 25, No. 3. (Year: 2005).*
U.S. Appl. No. 15/412,706, filed Jan. 23, 2017, R. Charles Murray et al.

* cited by examiner

*Primary Examiner* — Aaron J Kosar
(74) *Attorney, Agent, or Firm* — Dinsmore & Shohl LLP

(57) ABSTRACT

A topical mosquito control product includes active and inert ingredients. The active ingredients include natural materials and may include soybean oil, geraniol, cinnamon oil and cedar wood oil. The inert ingredients include natural materials and may include bee's wax, isopropyl alcohol, sunflower oil, salt, triethyl citrate and water.

3 Claims, 8 Drawing Sheets

TOPICAL MOSQUITO CONTROL PRODUCT

CROSS-REFERENCE TO RELATED APPLICATIONS

The instant application is a CIP application of U.S. application Ser. No. 15/412,706 filed on Jan. 23, 2017 which claims priority to U.S. Provisional Application Ser. No. 62/281,347 filed Jan. 21, 2016 and U.S. Provisional Application Ser. No. 62/416,457 filed Nov. 2, 2016 the entire contents of which are incorporated herein by reference.

FIELD OF THE INVENTION

The instant application is directed to a formulation for a topical mosquito repellent.

BACKGROUND OF THE INVENTION

Mosquito bites often cause annoying reactions in humans and animals. Additionally, mosquito bites are a vector for many types of disease including: malaria, Dengue Fever, Chikungunya, West Nile and Zika viruses as well as other forms of disease.

There is a need to prevent mosquitos from biting a host to lessen the discomfort of a bite reaction and to prevent the potential spread of a disease.

Accordingly, a natural non-toxic ingredient based topical product that prevents bites to humans and animals would be desirable.

SUMMARY OF THE INVENTION

In one aspect, there is disclosed a topical mosquito control product that includes active and inert ingredients. The active ingredients include soybean oil, cinnamon oil, cedar wood oil and geraniol and the inert ingredients include bee's wax, sunflower oil, triethyl citrate, water and isopropyl alcohol.

Also disclosed is a method of repelling insects which includes applying the lotion compositions to a body and exposing insects to the lotion.

Additional features and advantages of mosquito control products described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein and together with the description serve to explain the principles and operations of the claimed subject matter.

DETAILED DESCRIPTION OF THE EMBODIMENTS

Figure 1:
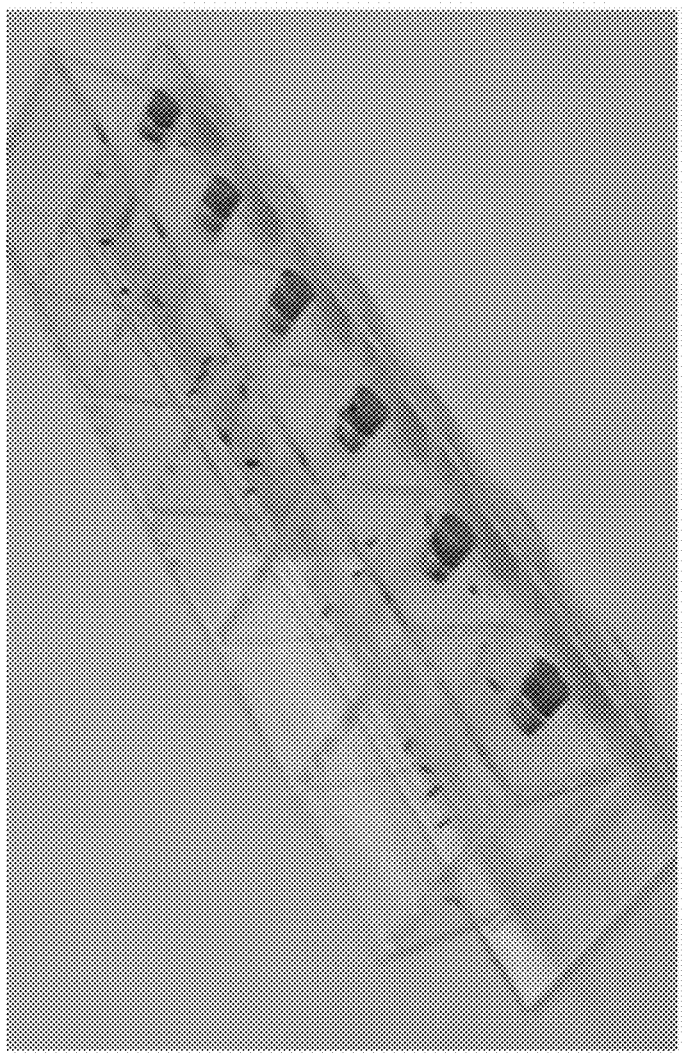
FIG. 1 is a graphical representation of an experimental apparatus used for testing.

Mosquito bites may transmit diseases and cause reactions to people that are bitten. Various repellant compositions have been utilized in prior art repellant compositions. One such repellant, DEET, is often used in mosquito repellant compositions. DEET has been questioned as to its toxicity in higher amounts for use with humans and other subjects. There is therefore a need in the art for an improved and safe topical mosquito repellant composition.

In one aspect, there is disclosed herein a formulation that may be utilized as a topical lotion or spray to repel mosquitos. The formulation may include organic and chemical-free compositions that will protect humans and other animals from blood-seeking insects such as mosquitos.

Example 1

In one aspect the composition may include shea, soybean oil, isopropyl alcohol, anise oil, citronella oil, and basil oil. The shea may be present in an amount of from 50 to 70% by weight. The soybean oil may be present in an amount of from 10 to 30% by weight. The isopropyl alcohol may be present from 5 to 15% by weight. The anise oil may be dispersed in a solvent such as isopropyl alcohol and may be present from 1.5 to 2.5% or at about 2% by weight. The citronella oil and basil oil may also be present in an amount of from 1.5 to 2.5% or at about 2% by weight. The weight percentages are based on a total weight of the composition.

As described above, the composition may include active ingredients and inactive ingredients. The soybean oil and citronella oil may be classified as active ingredients wherein the shea, isopropyl alcohol, anise oil, and basil oil may be considered inert or inactive ingredients.

Example 2

In an alternate composition, the shea may be replaced by beeswax. As described above, the shea had a 3 to 1 ratio with respect to the soy oil. However, the beeswax may have an alternate ratio with respect to the soy oil. In one aspect, the beeswax may be present in a 1 to 8 ratio with respect to the soy oil.

The composition may be formed by heating the soy oil to approximately 140° F. Next, the shea or beeswax is added to the composition. Next, the citronella oil, basil oil, and anise oils are added to the composition and mixed thoroughly. The composition is then allowed to cool to room temperature forming a stiff mass. Next, the composition is blended with a lotion substrate to form a cream lotion or spray. Various ratios of the composition and substrate may be utilized, for example a ratio of 50 to 4, 48 to 6, and 50 to 8 may be utilized with respect to the composition and the substrate cream component.

Example 3

In another aspect, the composition may include bee's wax, soybean oil, edible oil such as avocado oil or sunflower oil, isopropyl alcohol, peppermint oil, citronella oil, and thyme oil. The bee's wax may be present in an amount of from 10 to 20% by weight. The soybean oil may be present in an amount of from 40 to 60% by weight. The avocado oil may be present in an amount of from 20 to 35% by weight. The isopropyl alcohol may be present from 5 to 15% by weight. The peppermint oil may be present at about 1% by weight. The citronella oil may also be present in an amount of from 1.5 to 2.5% or 2% by weight. The thyme oil may be present at about 0.5% by weight. Additionally, the composition may include powdered ingredients such as vanillin present at about 0.4% by weight and Lecithin present at about 0.1% by weight. The weight percentages are based on a total weight of the composition.

As described above, the composition may include active ingredients and inactive ingredients. The soybean oil, peppermint oil, thyme oil and citronella oil may be classified as active ingredients wherein the bee's wax, avocado oil and isopropyl alcohol may be considered inert or inactive ingredients.

The composition of example 3 was made according to the following procedure. The soybean oil and sunflower oils were heated from room temperature to 145 to 160 degrees F. in a mixing vat under agitation. The vanillin, lecithin and bee's wax were added to the composition when the temperature approaches 100 F. The mixture is heated and agitated until the mixture clears. Once the mixture clears heat is removed from the composition. Isopropyl alcohol is added at the temperature of 110 F. The mixture immediately cools to 100 F. At this time the peppermint oil, citronella oil, and thyme oil are added to the composition. The composition is agitated and sheared for 30 minutes. After which time the lotion may be packaged.

Example 4

In another aspect, the composition may include the following formula:

|  | Percentage by weight | Density | Weight |  |
|---|---|---|---|---|
| Ingredient Active |  |  |  |  |
| Soybean Oil | 27.5 | 0.915 | 25.1625 | PLUS-MINUS 35% |
| Citronella Oil | 4 | 0.855 | 3.42 | PLUS-MINUS 40% |
| Cinnamon Oil | 4 | 1.04 | 4.16 | PLUS-MINUS 40% |
| Cedar Wood Oil | 4 | 0.952 | 3.808 | PLUS-MINUS 40% |
| Ingredient Inert |  |  |  |  |
| Sunflower Oil | 24 | 0.924 | 22.176 | PLUS-MINUS 35% |
| Turmeric | 4 | 0.92 | 3.68 | PLUS-MINUS 40% |

-continued

|  | Percentage by weight | Density | Weight |  |
|---|---|---|---|---|
| Anise | 3 | 0.98 | 2.94 | PLUS-MINUS 20% |
| Basil Oil | 4 | 0.895 | 3.58 | PLUS-MINUS 25% |
| Beeswax | 11 | 0.96 | 10.56 | PLUS-MINUS 30% |
| Salt | 1 | 2.165 | 2.165 | PLUS-MINUS 20% |
| Ethyl Ester | 3.3 | 1.04 | 3.432 | PLUS-MINUS 15% |
| Isopropyl Alcohol | 3 | 0.785 | 2.355 | PLUS-MINUS 20% |
| Water | 2 | 1 | 2 | PLUS-MINUS 35% |
| Vanillin | 5 | 1.06 | 5.3 | PLUS-MINUS 40% |
| Lecithin | 0.2 | 1.03 | 0.206 | PLUS-MINUS 25% |

The composition may include bee's wax, soybean oil, edible oil such as sunflower oil, isopropyl alcohol, cinnamon oil, cedar wood oil, citronella oil, turmeric, anise, basil oil, salt, ethyl ester, and water. The bee's wax may be present in an amount of from 10 to 20% by weight. The soybean oil may be present in an amount of from 10 to 60% by weight. The sunflower oil may be present in an amount of from 20 to 35% by weight. The isopropyl alcohol may be present from 2 to 10% by weight. The cinnamon oil may be present at about 2 to 10% by weight. The citronella oil may also be present in an amount of from 2% to 10% by weight. The cedar wood oil may be present in an amount of from 2% to 10% by weight. The turmeric may be present in an amount of from 2% to 10% by weight. The anise may be present in an amount of from 2% to 10% by weight. The basil oil may be present in an amount of from 2% to 10% by weight. Salt may be present in an amount of from 1% to 3% by weight. The ethyl ester may be present in an amount of from 2% to 10% by weight. Water may be present in an amount of from 1 to 4% by weight. Additionally, the composition may include powdered ingredients such as vanillin present at about 5% by weight and Lecithin present at about 0.2% by weight. The weight percentages are based on a total weight of the composition.

As described above, the composition may include active ingredients and inactive ingredients. The soybean oil, cinnamon oil, cedar wood oil and citronella oil may be classified as active ingredients wherein the bee's wax, sunflower oil, turmeric, anise oil, basil oil, salt, ethyl ester, water, vanillin, lecithin and isopropyl alcohol may be considered inert or inactive ingredients.

The composition of example 4 was made according to the following procedure. The soybean oil and sunflower oils were heated from room temperature to 145 to 160 degrees F. in a mixing vat under agitation. The vanillin, lecithin and bee's wax were added to the composition when the temperature approaches 100 F. The mixture is heated and agitated until the mixture clears. Once the mixture clears heat is removed from the composition. Water is then added to the composition under agitation and the composition is cooled to 110 F. Isopropyl alcohol is added at the temperature of 110 F. The mixture immediately cools to 100 F. At this time the cinnamon oil, cedar wood oil, turmeric, anise oil, basil oil, ethyl ester and an emulsion of salt water and citronella oil are added to the composition. The emulsion includes a 3.5% salt water mixture mixed at a ratio of 4 to 1 with the citronella oil. The composition is agitated and sheared for 30 minutes. After which time the lotion may be packaged.

Example 5

In another aspect, the composition may include the following formula:

| | Percentage by weight | Density | Weight | |
|---|---|---|---|---|
| Ingredient Active | | | | |
| Soybean Oil | 30.5 | 0.915 | 27.9075 | PLUS-MINUS 35% |
| Geraniol | 6 | 0.855 | 5.13 | PLUS-MINUS 40% |
| Cinnamon Oil | 5 | 1.04 | 5.2 | PLUS-MINUS 40% |
| Cedar Wood Oil | 4 | 0.952 | 3.808 | PLUS-MINUS 40% |
| Ingredient Inert | | | | |
| Sunflower Oil | 24 | 0.924 | 22.176 | PLUS-MINUS 35% |
| Beeswax | 12 | 0.96 | 11.52 | PLUS-MINUS 30% |
| Salt | 0.5 | 2.165 | 1.0825 | PLUS-MINUS 20% |
| Triethyl Citrate | 8 | 1.04 | 8.32 | PLUS-MINUS 15% |
| Isopropyl Alcohol | 2 | 0.785 | 1.57 | PLUS-MINUS 20% |
| Water | 2 | 1 | 2 | PLUS-MINUS 35% |
| Vanillin | 5.8 | 1.06 | 6.148 | PLUS-MINUS 40% |
| Lecithin | 0.2 | 1.03 | 0.206 | PLUS-MINUS 25% |

The composition may include bee's wax, soybean oil, edible oil such as sunflower oil, isopropyl alcohol, cinnamon oil, cedar wood oil, Geraniol, salt, triethyl citrate, and water. The bee's wax may be present in an amount of from 8 to 16% by weight. The soybean oil may be present in an amount of from 10 to 60% by weight. The sunflower oil may be present in an amount of from 20 to 40% by weight. The isopropyl alcohol may be present from 1 to 4% by weight. The cinnamon oil may be present at about 2 to 10% by weight. The Geraniol may also be present in an amount of from 3% to 10% by weight. The cedar wood oil may be present in an amount of from 2% to 8% by weight. Salt may be present in an amount of from 0.5% to 2% by weight. The triethyl citrate may be present in an amount of from 6% to 10% by weight. Water may be present in an amount of from 1 to 4% by weight. Additionally, the composition may include powdered ingredients such as vanillin present at about 5% by weight and Lecithin present at about 0.2% by weight. The weight percentages are based on a total weight of the composition.

As described above, the composition may include active ingredients and inactive ingredients. The soybean oil, cinnamon oil, cedar wood oil and Geraniol may be classified as active ingredients wherein the bee's wax, sunflower oil, salt, triethyl citrate, water, vanillin, lecithin and isopropyl alcohol may be considered inert or inactive ingredients.

The composition of example 5 was made according to the following procedure. The soybean oil and sunflower oils were heated from room temperature to 145 to 160 degrees F. in a mixing vat under agitation. The vanillin, lecithin and bee's wax were added to the composition when the temperature approaches 100 F. The mixture is heated and agitated until the mixture clears. Once the mixture clears heat is removed from the composition. Water is then added to the composition under agitation and the composition is cooled to 120 F. Isopropyl alcohol is added at the temperature of 120 F. The mixture immediately cools to 100 F. At this time the cinnamon oil, cedar wood oil, triethyl citrate and an emulsion of salt water and Geraniol are added to the composition. The emulsion includes a 25% salt water mixture mixed at a ratio of 4 to 1 with the Geraniol. The composition is agitated and sheared for 30 minutes. After which time the lotion may be packaged.

Figure 2:
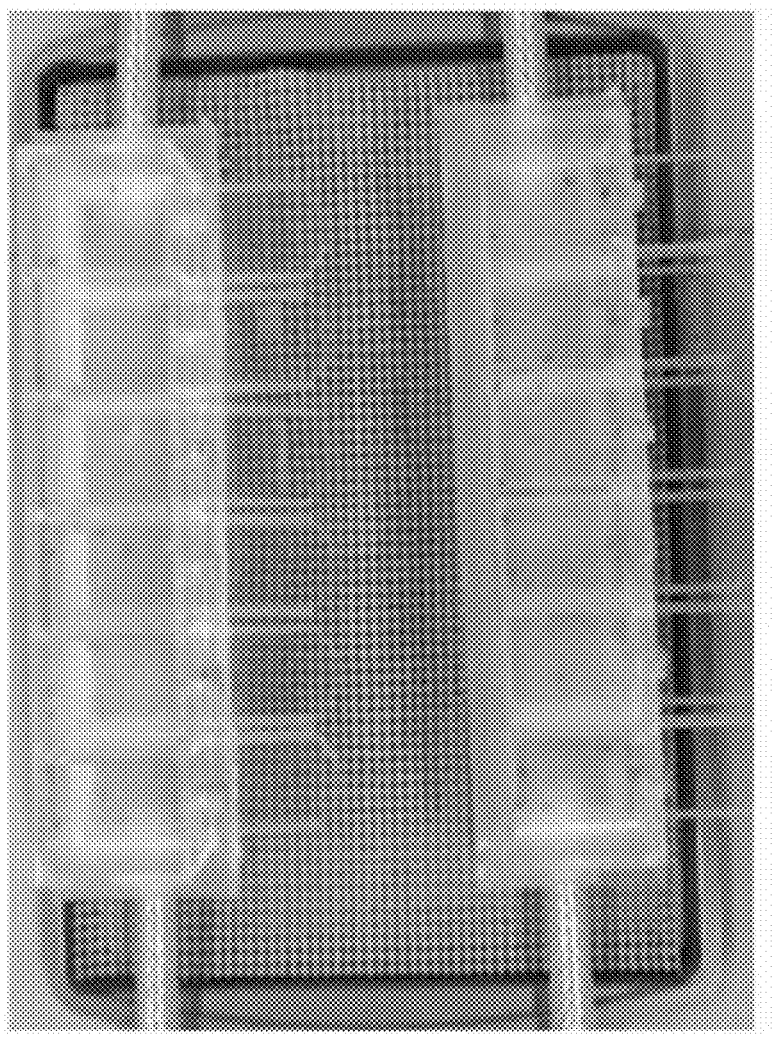
FIG. 2 is a graphical depiction of an experimental apparatus positioned over a blood source.
Figure 3:
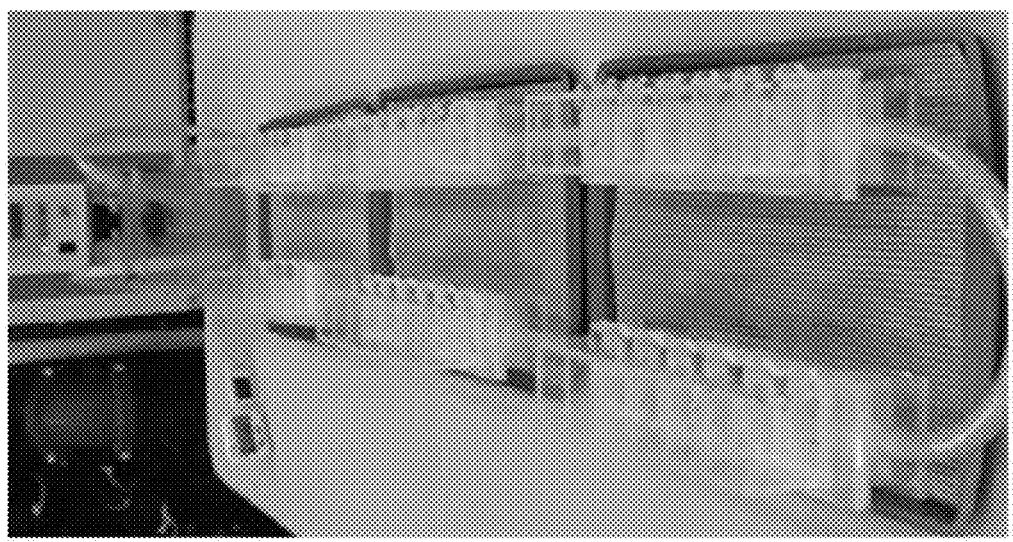
FIG. 3 is a graphical representation of an experimental apparatus including a circulating pump providing warm water to the testing apparatus.

The deterrent effect of the above-described compositions of examples 1-3 was tested in a controlled environment. In vitro laboratory tests were conducted and measured and compared to DEET and nontreated control groups for yellow fever mosquitos, *Aedes aegypti*. Bioassays were conducted in nine six-chambered Plexiglas K & D modules stocked with female *Aedes aegypti* mosquitos as shown in FIGS. 1-3. Five female mosquitos were aspirated into each of the six chambers of the nine modules. Repellant treatments were applied at 26.7 microliters with a pipette and spread with a small brush over 12 square centimeter sections of organdy cloth attached to a flat plastic template containing rectangular openings. The treated cloth covered template was fitted between the K & D module and a lower Plexiglas unit. The lower Plexiglas unit contained shallow surface wells filled with a blood substitute (CDTA and ATP) and covered with a moistened collagen membrane. The blood substitute was heated to 38° C. using water pumped through hose lines attached to the lower units and a water bath supplied with a temperature controlled inversion circulator. Mosquitos were exposed to the treated surfaces by opening sliding doors beneath the modules for 90-second biting counts at five post-treatment time intervals from 1 to 6 hours. Fresh, untreated mosquitos are used for each time interval.

The bite counts were tabulated and utilized for statistical analysis. The percent repellency of the formulations as described above was more effective than DEET over the five time periods. At the initial start time of zero the repellency of the composition as described herein was 100% while DEET was 91.9%. The average for all five time periods demonstrates the repellency of 94.54% for the compositions as described herein compared to 86.52% for DEET. At the 6 hour time period the compositions as described herein included a repellency of 96.8% effective compared to DEET which was 87.1% effective.

The testing protocol including the in vitro environment provides a rigorous testing of the repellency of the composition as the mosquitos are confined with a blood meal.

An unpaired t-test was conducted on the biting counts between lotion as described herein and the control group where there was no treatment applied between the mosquito and the blood well. The results of this test showed highly significant results between the mean biting counts of 0.33 for the compositions as described herein compared to 3.44 for the control group. The statistical factors include t=5.8704 where df=16 and a standard error of difference is equal to 0.530. The two-tailed p value is less than 0.0001. The reduction in biting pressure when using the compositions compared to the control group is significant at the 99.99 level of significance.

The experimental results demonstrate a very high effectiveness of repellency utilizing a safe and effective organic product that is both DEET and chemical free. The testing has demonstrated that the product is effective in repelling mosquitos and in particular the yellow fever mosquito which may potentially carry West Nile virus.

Additional testing was performed with the lotion formula of example 4 including: bee's wax, soybean oil, edible oil such as sunflower oil, isopropyl alcohol, cinnamon oil, cedar wood oil, citronella oil, turmeric, anise, basil oil, salt, ethyl ester, and water with the following protocols. *Aedes aegypti* mosquitoes were obtained from insecticide-susceptible reference strains held at the London School of Hygiene & Tropical Medicine, UK. All mosquitoes are reared and housed under optimal environmental conditions of 25° C.±2° C. and 80% Relative Humidity with a 12:12 hour photoperiod. Testing was carried out in a testing room maintained at 25±2K and 80% RH with a 12:12 hour photoperiod. For each product, the same person carried out the arm-in-cage testing.

For each product test, three batches of 50 female mosquitoes were placed in cages 30×30×30 cm inside the testing room. Before the start of each test a bare arm with gloved hand was inserted into the cage for 30 seconds to assess the biting readiness of the mosquitoes. Only cages with at least ten mosquitoes landing within 30 seconds were used in subsequent testing. The number of mosquitoes probing the untreated arm was counted at the end of the 30 second test. Following the combined fitness/control test, the product was applied onto the right arm at the WHO standard rate of 1 ml per 600 cm2 (1.6711 per cm2) for the Mosquito Insect Repellent and DEET, and at a rate of 2 mg per cm' for the Sunscreen Repellent. The arm was then inserted into the cage for 30 seconds and the number of mosquitoes probing on the arm counted and recorded. The procedure was repeated with a total of three cages. This was repeated for each of the three cages and at hourly intervals until 8 hours post-application or until protection drops below 50%. Each product was tested on a separate test day.

Protective efficacy (PE) was calculated using the following formula: PE=(Mosquitoes probing on control arm−Mosquitoes probing on treated arm)/Mosquitoes probing on control arm×100. The average probing on the control arm during testing was 16, 17 and 21 mosquitoes at the end of the 30 second exposure time, in cages used for testing the Mosquito Insect Repellent Lotion and 8% DEET respectively. The Mosquito Insect Repellent Lotion 100% protection at 0 hours, whereas the 8% DEET provided 100% protection for 1 hour after application (Table 1). The Mosquito Insect Repellent Lotion provided over 50% protection for, 3 hours, whereas 8% DEET provided over 50% protection for 6 hours.

TABLE 1

Total Protective Efficacy of the Mosquito Insect Repellent Lotion against *Aedes aegypti* mosquitos

| Hours after Application | Time (hh:mm) | Replicate | No. probing on bare control arm | No. probing on treated arm | % PE | Total % PE |
|---|---|---|---|---|---|---|
| 0 | 10:44 | 1 | 13 | 0 | 100.00 | 100.00 |
|   |   | 2 | 15 | 0 | 100.00 |   |
|   |   | 3 | 12 | 0 | 100.00 |   |
| 1 | 11:43 | 1 | 10 | 1 | 90.00 | 90.91 |
|   |   | 2 | 16 | 1 | 93.75 |   |
|   |   | 3 | 18 | 2 | 88.89 |   |
| 2 | 12:48 | 1 | 12 | 0 | 100.00 | 86.96 |
|   |   | 2 | 15 | 2 | 86.67 |   |
|   |   | 3 | 19 | 4 | 78.95 |   |
| 3 | 13:43 | 1 | 14 | 5 | 64.29 | 62.22 |
|   |   | 2 | 12 | 5 | 58.33 |   |
|   |   | 3 | 19 | 7 | 63.16 |   |
| 4 | 14:45 | 1 | 16 | 6 | 62.50 | 47.83 |
|   |   | 2 | 18 | 10 | 44.44 |   |
|   |   | 3 | 12 | 8 | 33.33 |   |
| 5 | 15:45 | 1 | 17 | 13 | 23.53 | 31.03 |
|   |   | 2 | 20 | 14 | 30.00 |   |
|   |   | 3 | 21 | 13 | 38.10 |   |

COMPARATIVE TABLE 2

Total Protective Efficacy of 8% DEET against *Aedes aegypti* mosquitos

| Hours after Application | Time (hh:mm) | Replicate | No. probing on bare control arm | No. probing on treated arm | % PE | Total % PE |
|---|---|---|---|---|---|---|
| 0 | 09:40 | 1 | 16 | 0 | 100.00 | 100.00 |
|   | 09:42 | 2 | 28 | 0 | 100.00 |   |
|   | 09:44 | 3 | 30 | 0 | 100.00 |   |
| 1 | 10:40 | 1 | 15 | 0 | 100.00 | 100.00 |
|   | 10:42 | 2 | 23 | 0 | 100.00 |   |
|   | 10:43 | 3 | 35 | 0 | 100.00 |   |
| 2 | 11:42 | 1 | 12 | 1 | 91.67 | 95.00 |
|   | 11:44 | 2 | 22 | 2 | 90.91 |   |
|   | 11:46 | 3 | 26 | 0 | 100.00 |   |
| 3 | 12:40 | 1 | ND | ND | — | 95.35 |
|   | 12:42 | 2 | 20 | 2 | 90.00 |   |
|   | 12:46 | 3 | 23 | 0 | 100.00 |   |
| 4 | 01:40 | 1 | 24 | 2 | 91.67 | 95.16 |
|   | 01:42 | 2 | 17 | 1 | 94.12 |   |
|   | 01:44 | 3 | 21 | 0 | 100.00 |   |
| 5 | 02:40 | 1 | 29 | 2 | 93.10 | 90.00 |
|   | 02:42 | 2 | 18 | 2 | 88.89 |   |
|   | 02:44 | 3 | 23 | 3 | 86.96 |   |
| 6 | 03:40 | 1 | 17 | 10 | 41.18 | 54.90 |
|   | 03:42 | 2 | 14 | 6 | 57.14 |   |
|   | 03:44 | 3 | 20 | 7 | 65.00 |   |

COMPARATIVE TABLE 2-continued

Total Protective Efficacy of 8% DEET against *Aedes aegypti* mosquitos

| Hours after Application | Time (hh:mm) | Replicate | No. probing on bare control arm | No. probing on treated arm | % PE | Total % PE |
|---|---|---|---|---|---|---|
| 7 | 04:40 | 1 | 11 | 7 | 36.36 | 46.34 |
|   | 04:42 | 2 | 12 | 6 | 50.00 |   |
|   | 04:44 | 3 | 18 | 9 | 50.00 |   |

Additional Testing

Additional Field Testing of the Lotion Formulations was Performed.

Sarasota, Fla.

Two years of testing in a swamp-type environment in central Sarasota, Fla. from 2014 through 2016 yield 100% effectiveness in a natural environmental setting with high mosquito infestation. After application of the lotion of examples 1-4 as presented in the embodiments disclosed above, it was observed that the repellency is 100% and with no application of the product the number of bites normally exceeds 10 in a 5 minute exposure.

Company personnel camping in Myakka State Park in central Florida have tested the lotions over numerous overnight camping trips over the past 2 years (2014 to 2016). The Myakka River flows through 57 square miles of wetlands and prairies and may rival the Cagayan Region in northern Luzon in the Philippines for mosquito population densities. During these field tests the personnel report 100% success in repellency.

Tauo, Cagayan Valley, Philippines

During January of 2016 concrete workers on the edge of flooded rice fields in Tauo were given the lotion of the embodiments of examples 1-4 described above. During an 8 hour day these workers reported no bites, or 100% repellency. Other tile and wood workers at the same location working on the project were given no repellent and experienced scores of bites. For the following days of the construction project all workers were given the lotion and no workers reported bites.

Figure 4:
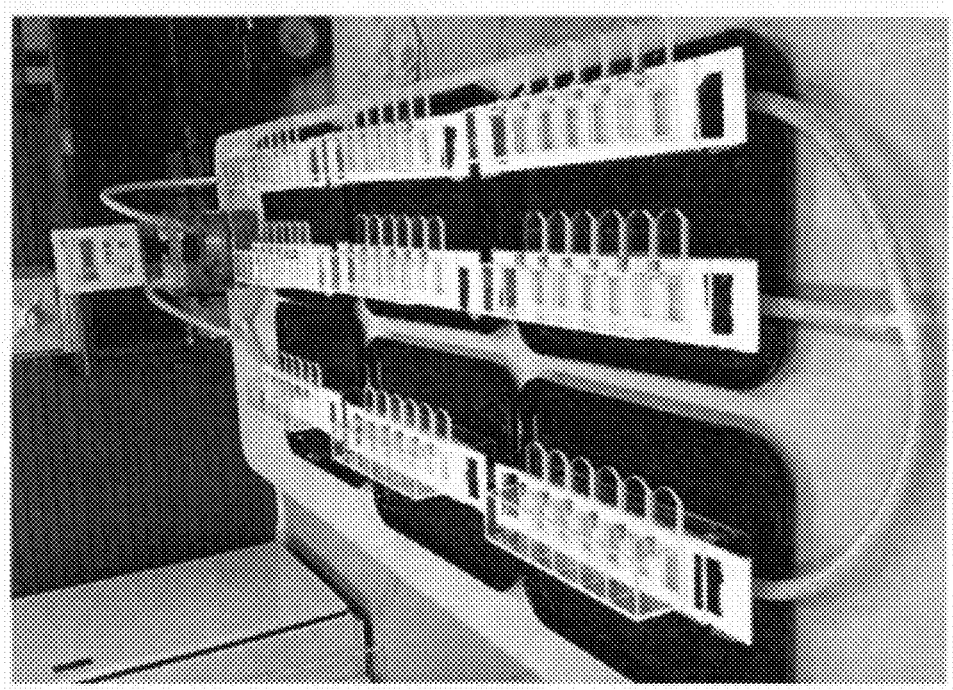
FIG. 4 is a graphical depiction of an experimental apparatus positioned over a blood source.
Figure 5:
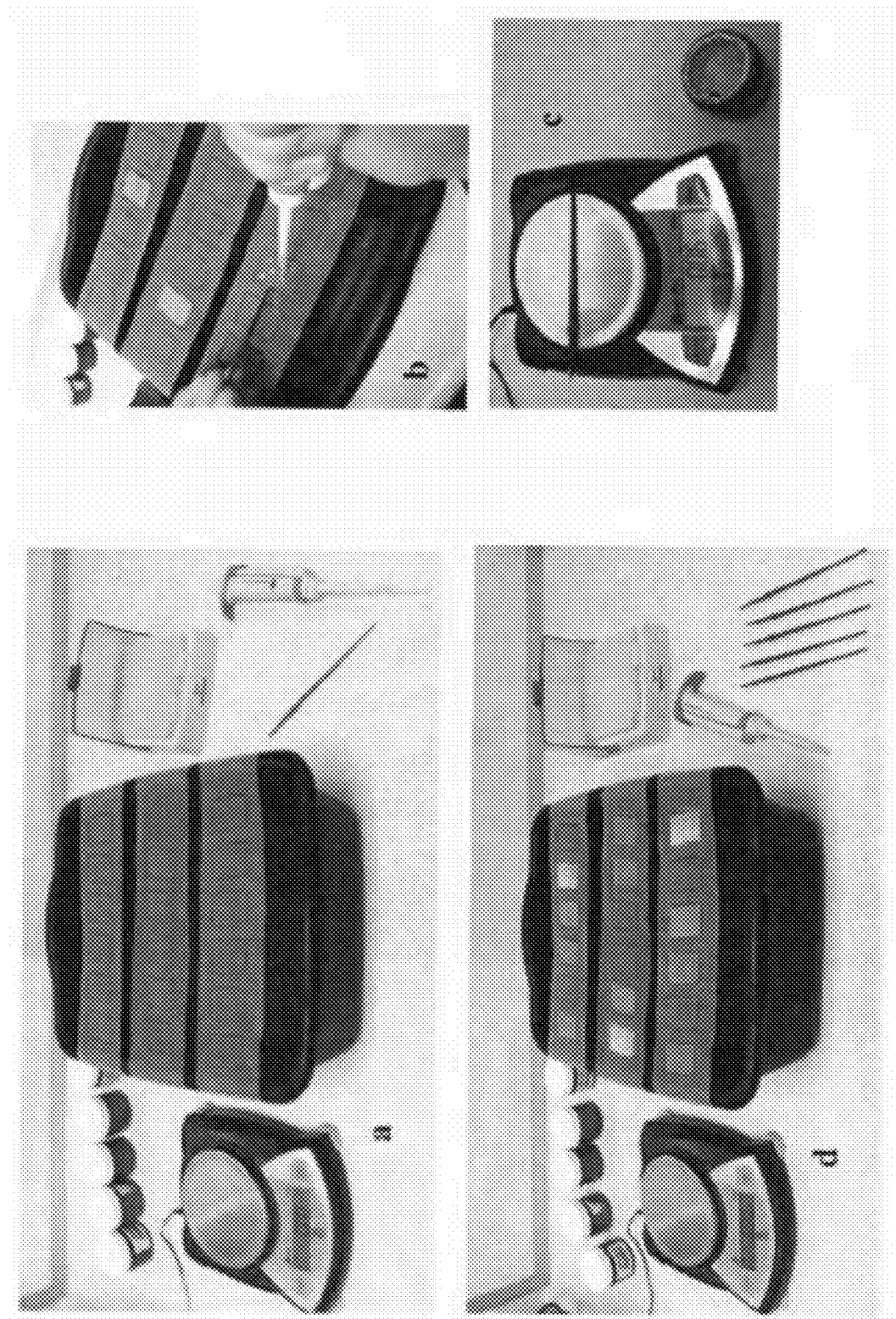
FIG. 5 is a graphical depiction of an experimental apparatus and application of repellents.
Figure 6:
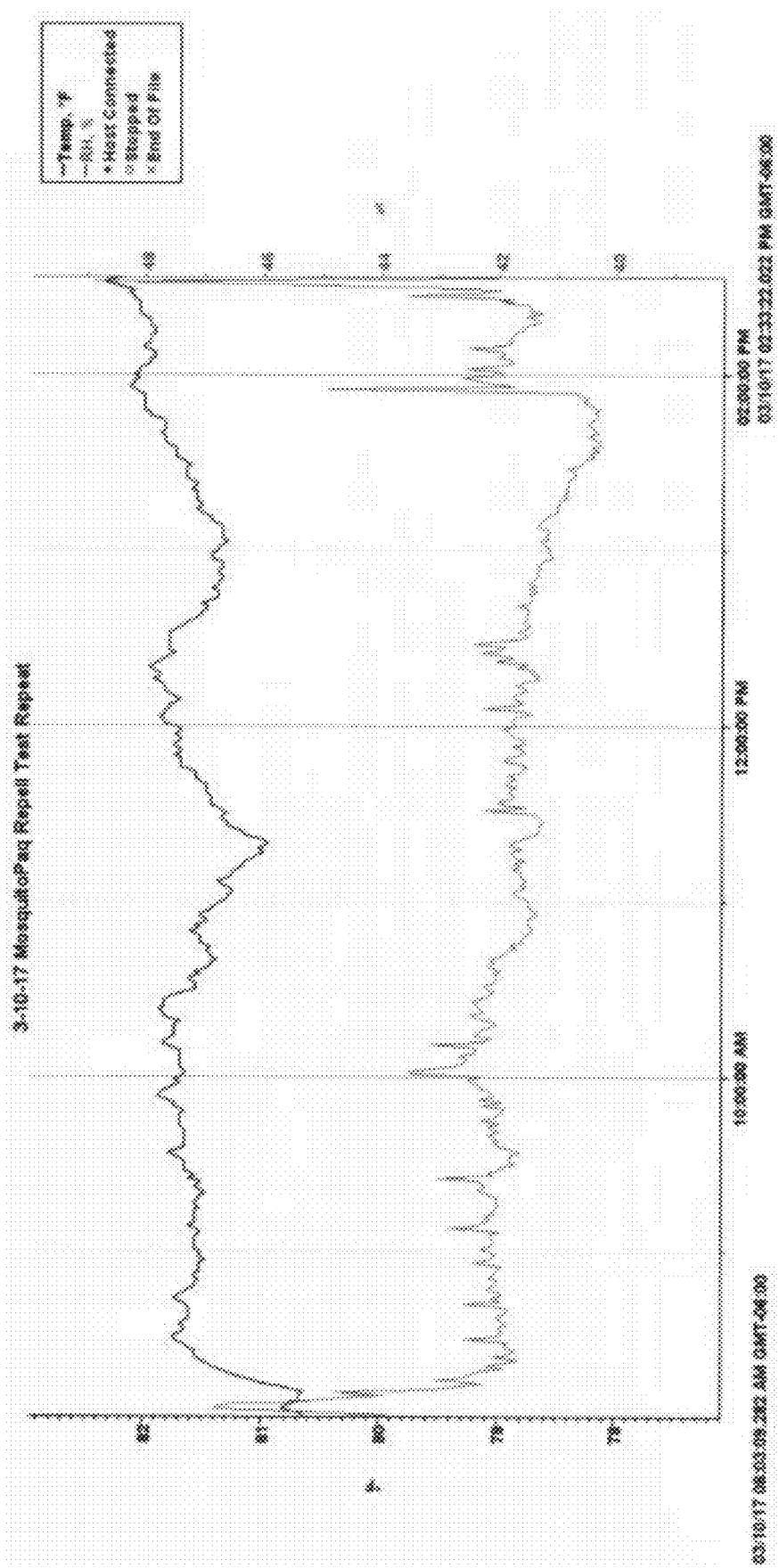
FIG. 6 is a graphical depiction of the temperature and humidity readings of example 5.

The deterrent effect of the above-described compositions of example 5 (represented as NO-Bite in FIGS. 7-8) was tested in a controlled environment. In vitro laboratory tests were conducted and measured and compared to DEET and nontreated control groups for yellow fever mosquitos, *Aedes aegypti*. The repellency of the formulations were compared to a DEET standard, and a non-treated control against yellow fever mosquitoes, *Aedes aegypti*. The examples were performed in a temperature-controlled laboratory following techniques as disclosed in Klun, J. A., M. A. Kramer, A. Zhang, S. Wang, and M. Debboun. 2008. A quantitative in vitro assay for mosquito deterrent activity without human blood cells. J Am. Mosq. Contr. Assoc. 24:508-512. Bioassays were conducted in nine, six-chambered Plexiglasss K&D modules interconnected with hoses to a water bath supplied with a temperature-controlled inversion circulator as displayed in (FIG. 4). Five colony-reared female *Aedes aegypti* were aspirated into each chamber (FIG. 1). Nine replications of the following treatments were randomly assigned to the chambers: No-Bite; No-Burn; Positive control—7% DEET standard (Off! Family Care Unscented) and Negative control—Non-treated. Repellents were applied to nine ca. 2"×2"×9" strips of organdy cloth and spread with a small paint brush over 12 cm' ink-pen-demarcated rectangles drawn on the strips with a flat plastic template. A micropipette set at 27.6 µl was used to apply liquid repellents, while creams were applied at 0.06 g (FIG. 5 a-d). Treated clothes were taped to flat plastic templates with openings aligning with lower Plexiglasss bases. The lower Plexiglasss bases contained shallow surface wells that were filled with a blood substitute (CDTA and ATP) and covered with moistened collagen membranes. The blood substitute was heated to 38° C. with water pumped through hose lines attached to the lower base and the water bath. The plastic templates were fitted between the K&D modules and lower Plexiglasss bases (FIG. 4). Mosquitoes were exposed to the treated surfaces by opening the K&D module sliding doors for 90-second biting counts at five post-treatment time intervals (0, 1, 2, 4 & 6 hrs) (FIG. 1). Fresh mosquitoes were aspirated into the chambers for each time interval. Ambient temperature and humidity were continuously recorded throughout the study with a HOBO data logger as displayed in FIG. 6. The dependent variable was biting count mean. Treatment and module means were independent variables. Biting counts as well as log and square root transformed biting counts by treatment were examined for normality with SAS PC Proc Univariate. The variance in biting count means by treatment and time intervals was statistically analyzed with SAS Proc ANOVA and statistically tested for significant differences with Tukey's Studentized Range test at $p<0.05$ and charted with 95% Confidence Intervals (C.I.). Average % repellency was calculated with the following formula and charted by treatment and time interval: (Control Avg. Biting Count−Treatment Avg. Biting Count)÷Control Avg. Biting Count×100.

Normality Tests:

Biting counts by treatment were found to follow closer to a normal distribution compared to log or square root transformed data. Consequently, all statistical analysis was conducted on non-transformed data.

Figure 7:
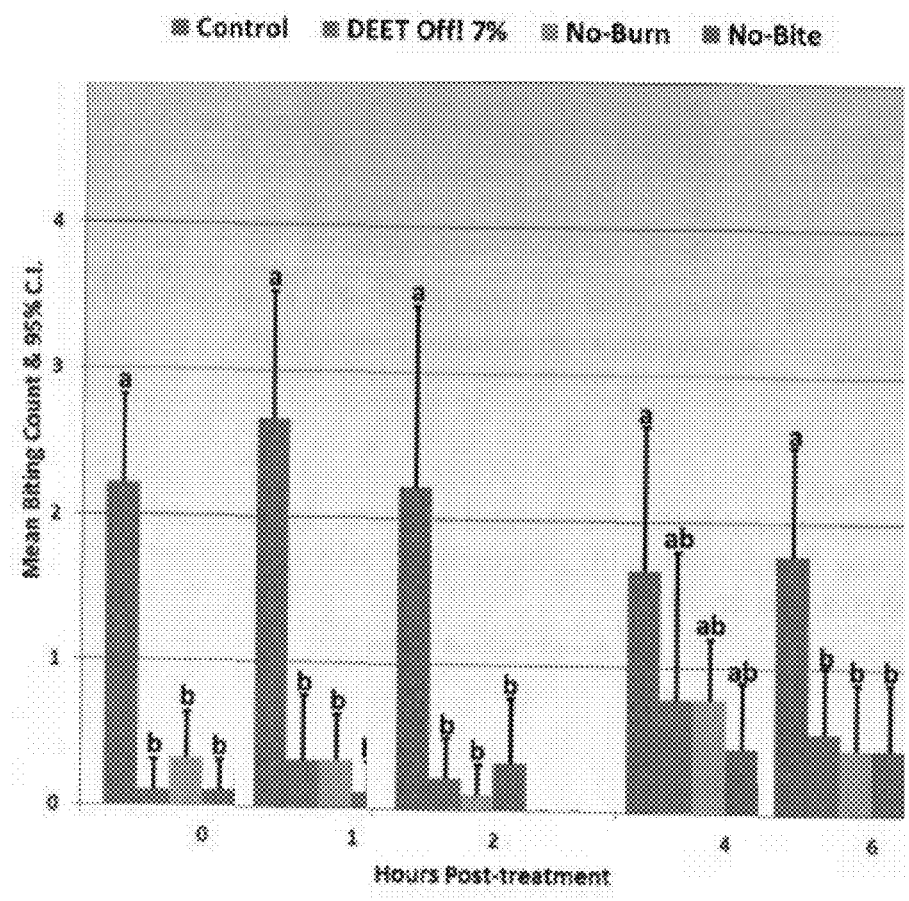
FIG. 7 is a graph of the mean bite count as a function of time for repellents of example 5.
Figure 8:
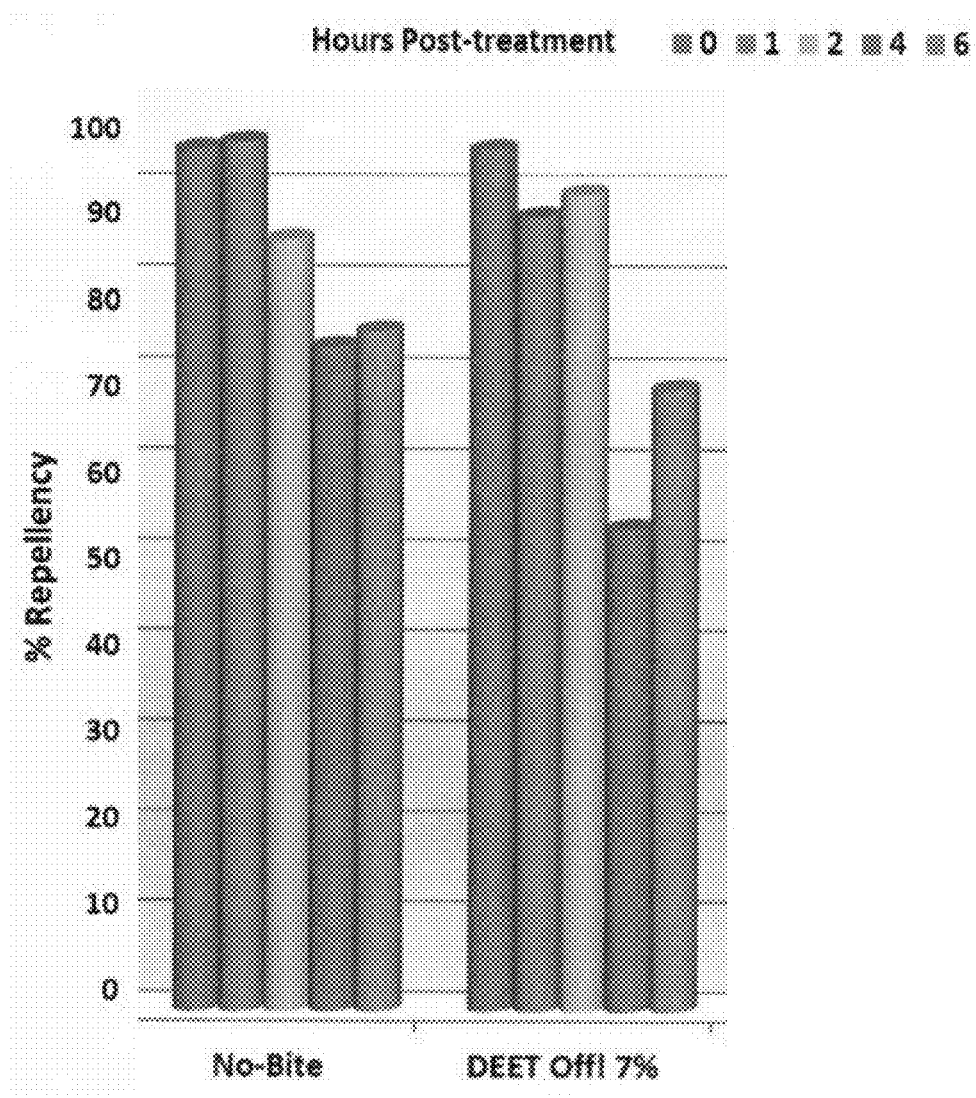
FIG. 8 is a graph of the % repellency as a function of time for repellents of example 5.

Biting Count and Repellency:

There was no significant difference ($p>0.05$) in average biting counts among the nine K&D modules. Biting counts in the controls were significantly ($p<0.05$) greater than all of the repellent treatments at 0, 1, 2, and 6 hours post-treatment (FIG. 7). At 4-hours, there was no significance difference ($p>0.05$) in biting activity among the control, DEET and no-burn/no-bite. There was no significant difference ($p>0.05$) in bites among the repellents at 4 hours. When biting count data were converted to percent repellency, all of the formulations appeared to perform as well, if not better, than the 7% DEET (FIG. 8).

We claim:

1. A topical mosquito repellent composition comprising:
   a lotion including active and inert ingredients, wherein the active ingredients include soybean oil, cinnamon oil, cedar wood oil and geraniol and the inert ingredients include bee's wax, sunflower oil, salt, triethyl citrate, water and isopropyl alcohol;
   wherein the bee's wax is present in an amount of from 8 to 16% by weight, the soybean oil is present in an amount of from 10 to 60% by weight, the sunflower oil is present in an amount of from 20 to 40% by weight, the isopropyl alcohol is present from 1 to 4% by weight, the cinnamon oil is present in an amount of from 2 to 10% by weight, the geraniol is present in an amount of from 3% to 10% by weight, the cedar wood oil is present in an amount of from 2% to 8% by weight, salt is present in an amount of from 0.5% to 2% by weight, triethyl citrate is present in an amount of from 6% to 10% by weight, water is present in an amount of from 1 to 4% by weight.

2. The topical mosquito repellent composition of claim 1 wherein the inert ingredients further includes powdered ingredients including vanillin and lecithin.

3. The topical mosquito repellent composition of claim 2 wherein the vanillin is present in an amount of about 5% by weight and lecithin is present in an amount of about 0.2% by weight.

* * * * *